United States Patent
Yi et al.

(10) Patent No.: US 12,308,107 B2
(45) Date of Patent: May 20, 2025

(54) MEDICAL IMAGE DIAGNOSIS ASSISTANCE APPARATUS AND METHOD FOR PROVIDING USER-PREFERRED STYLE BASED ON MEDICAL ARTIFICIAL NEURAL NETWORK

(71) Applicant: Coreline Soft Co., Ltd., Seoul (KR)

(72) Inventors: Jaeyoun Yi, Seoul (KR); Donghoon Yu, Gimpo-si (KR); Yongjin Chang, Incheon (KR); Hyun Gi Seo, Goyang-si (KR)

(73) Assignee: Coreline Soft Co., Ltd., Seoul (KR)

( * ) Notice: Subject to any disclaimer, the term of this patent is extended or adjusted under 35 U.S.C. 154(b) by 868 days.

(21) Appl. No.: 17/130,669

(22) Filed: Dec. 22, 2020

(65) Prior Publication Data
US 2021/0202072 A1    Jul. 1, 2021

(30) Foreign Application Priority Data
Dec. 27, 2019   (KR) .................. 10-2019-0177122

(51) Int. Cl.
*G16H 30/20*    (2018.01)
*G06T 7/00*    (2017.01)
(Continued)

(52) U.S. Cl.
CPC .......... *G16H 30/20* (2018.01); *G06T 7/0014* (2013.01); *G16H 30/40* (2018.01); *G16H 50/20* (2018.01); *G16H 80/00* (2018.01)

(58) Field of Classification Search
CPC ........ G16H 30/20; G16H 30/40; G16H 50/20; G16H 80/00; G16H 50/70; G16H 70/60;
(Continued)

(56) References Cited

U.S. PATENT DOCUMENTS 8,165,368 B2    4/2012   Vijaykalyan et al.
8,923,580 B2    12/2014  Dekel et al.
(Continued)

FOREIGN PATENT DOCUMENTS

JP    2008-188214 A    8/2008
KR    101263705 B1    6/2013
(Continued)

*Primary Examiner* — Md K Talukder
(74) *Attorney, Agent, or Firm* — United One Law Group LLC; Kongsik Kim; Jhongwoo Peck

(57) ABSTRACT

Disclosed herein is an artificial neural network-based medical image diagnosis assistance apparatus for assisting in diagnosing a medical image based on a medical artificial neural network. A medical image diagnosis assistance apparatus according to an embodiment of the present invention includes a computing system, and the computing system includes at least one processor. The at least one processor is configured to acquire or receive a first analysis result obtained through the inference of a first artificial neural network about a first medical image, to detect user feedback on the first analysis result input by a user, to determine whether the first analysis result and the user feedback satisfy training conditions, and to transfer the first analysis result and the user feedback satisfying the training conditions to a style learning model so that the style learning model is trained on the first analysis result and the user feedback.

10 Claims, 8 Drawing Sheets

(51) Int. Cl.
*G16H 30/40* (2018.01)
*G16H 50/20* (2018.01)
*G16H 80/00* (2018.01)

(58) Field of Classification Search
CPC ....... G06T 7/0014; G06T 7/0012; G06T 7/10; G06V 10/70; G06V 10/25; G06V 10/82
See application file for complete search history.

(56) References Cited

U.S. PATENT DOCUMENTS

| | | | |
|---|---|---|---|
| 9,152,760 B2 | 10/2015 | Sherman et al. | |
| 9,773,305 B2 | 9/2017 | Lee et al. | |
| 10,192,551 B2* | 1/2019 | Carbune | G10L 15/063 |
| 2016/0209995 A1* | 7/2016 | Jeon | G16Z 99/00 |
| 2019/0156484 A1* | 5/2019 | Nye | G16H 30/20 |
| 2019/0164285 A1* | 5/2019 | Nye | G16H 10/60 |
| 2019/0205606 A1 | 7/2019 | Zhou et al. | |
| 2019/0294923 A1* | 9/2019 | Riley | G06F 18/24 |
| 2019/0371464 A1 | 12/2019 | Kim et al. | |
| 2021/0035287 A1* | 2/2021 | Kim | G06N 3/08 |
| 2021/0202072 A1* | 7/2021 | Yi | G16H 30/20 |
| 2022/0301159 A1* | 9/2022 | Byun | A61B 1/0005 |
| 2022/0366562 A1* | 11/2022 | Yu | G16H 30/40 |
| 2023/0108955 A1* | 4/2023 | Weissman | G16H 30/40 705/2 |

FOREIGN PATENT DOCUMENTS

| | | |
|---|---|---|
| KR | 10-2014-0091176 A | 7/2014 |
| KR | 10-2015-0006807 A | 1/2015 |
| KR | 101818074 B1 | 1/2018 |
| KR | 101880678 B1 | 7/2018 |
| KR | 101923962 B1 | 11/2018 |
| KR | 101943011 B1 | 1/2019 |

* cited by examiner

MEDICAL IMAGE DIAGNOSIS ASSISTANCE APPARATUS AND METHOD FOR PROVIDING USER-PREFERRED STYLE BASED ON MEDICAL ARTIFICIAL NEURAL NETWORK

CROSS-REFERENCE TO RELATED APPLICATION

This application claims under 35 U.S.C. § 119(a) the benefit of Korean Patent Application No. 10-2019-0177122 filed on Dec. 27, 2019, which is incorporated herein by reference in its entirety.

TECHNICAL FIELD

The present invention relates to an apparatus and method for assisting in reading and/or diagnosing a medical image of a subject. More particular, the present invention relates to a computing system for assisting in reading and/or diagnosing a medical image using the analysis result of a medical artificial neural network and also relates to software that is executed on the computing system.

The present invention was derived from the research conducted as part of the Robot Industry Core Technology R&D Project sponsored by the Korean Ministry of Trade, Industry and Energy and the Korea Evaluation Institute of Industrial Technology [Task Management Number: 1415162041; and Project Name: Development Of Commercialization Through Clinical Trials Of Interventional Robot System and Advancement Of Technology for Enhancement of Product Competitiveness].

BACKGROUND ART

Currently, medical images such as computed tomography (CT) images are widely used to analyze lesions and then use analysis results for diagnosis. For example, chest CT images are frequently used for diagnosis because they enable users to observe abnormalities inside the body such as the lungs, the bronchi, and the heart.

Some findings that can be diagnosed through chest CT images may be easily overlooked by human doctors because they are not easy to diagnose and even radiologists can distinguish their features and forms only after years of training. In particular, when the difficulty of diagnosis is high as in the diagnosis of a lung nodule, the case of overlooking a lesion may occur even when a doctor pays a high degree of attention, which may lead to trouble.

In order to assist in reading and/or diagnosing images that humans can easily overlook, the need for computer-aided diagnosis (CAD) has arisen. Conventional CAD technology is limited to assisting doctors in making decisions in a considerably limited area. For example, Korean Patent Application Publication No. 10-2014-0091176 and U.S. Pat. No. 9,773,305 disclose a conventional apparatus and method for assisting in diagnosing lesions.

In medical image segmentation, artificial neural network technology that detects and segments features in images that are easy to overlook with the human eye has been introduced. For example, U.S. Patent Application Publication No. 2019/0205606 entitled "Method and System for Artificial Intelligence Based Medical Image Segmentation" discloses a technology for segmenting a medical image using an artificial neural network.

For recent medical images such as CT images or magnetic resonance images (MRIs), a series of medical images is acquired through a single acquisition, and the series of medical images is not limited to only one type of lesion but can be used to detect various types of lesions.

CAD technology can provide a partially pre-completed analysis result to assist a doctor in reading and/or diagnosing a medical image. At a recent medical site, a doctor can review an analysis result provided by CAD technology and provide a diagnosis result based on the CAD analysis result. In addition, in the case of image segmentation technology, after a medical image has been segmented, a doctor may review an image segmentation result and may then proceed with a subsequent process or provide a diagnosis result.

Accordingly, an attempt has been made to increase the reliability of a diagnosis result by combining professional analysis with a decision assistance system, a CAD system, or an image segmentation engine based on artificial intelligence diagnosis. For example, Korean Patent No. 10-1818074 entitled "Artificial Intelligence-based Automatic Medical Diagnosis Assistance Method and System" discloses a prior art technology in which a host acquires a first diagnosis result based on artificial intelligence, a user input for the first diagnosis result is obtained, a second diagnosis result reflecting the user input is generated, and the second diagnosis result corresponding to the first diagnosis result is provided to the host.

In the prior art technology, lesion area information automatically detected by a CAD engine, area information added or modified by a user, and lesion diagnosis information deleted by the user are divided into separate layers and then stored. In addition, the second diagnosis result obtained by the user based on the first diagnosis result may be put into a database for the re-training or re-diagnosis of the CAD engine. Although the prior art technology has been mainly disclosed for the CAD engine, similar content may be applied to an image segmentation engine or a decision assistance system.

The prior art technologies may provide an infrastructure in which information added or modified by a user for primary analysis/segmentation/diagnosis information automatically detected or segmented by a CAD engine or image segmentation engine can be tracked and also provide an infrastructure in which the re-training or re-analysis/re-segmentation/re-diagnosis of the analysis/segmentation/diagnosis result can be supported. However, since there is no guarantee that accuracy will always be improved by the re-training of the CAD engine or image segmentation engine provided at an actual medical site, additional measures are required to increase the reliability of the CAD engine or image segmentation engine at a medical site.

SUMMARY OF THE DISCLOSURE

The accuracy of CAD or decision assistance systems that output segmentation, lesion detection, diagnosis, and finding results for medical images have been dramatically improved by utilizing artificial neural networks. However, since the accuracy is still not 100%, a diagnosis is being made at an actual medical site in such a manner that a radiologist or clinician reviews a first analysis result for a medical image obtained by an artificial neural network and generates a user modified analysis result reflecting user feedback that modifies or supplements the first analysis result.

Prior art technologies such as Korean Patent No. 10-1818074 entitled "Artificial Intelligence-based Automatic Medical Diagnosis Assistance Method and System" propose an attempt to improve the accuracy of an artificial neural network-based CAD engine in such a manner that a doctor, who is a user, reviews the lesion area information automatically detected by the artificial neural network-based CAD engine and a modified final diagnosis result is re-input to the artificial neural network-based CAD engine and then re-trained on.

However, a convolutional neural network (CNN), which has recently brought the rapid development of artificial neural network technology, has a configuration close to a black box to such an extent that it is impossible to know the way in which an inference is made therein from the outside, and thus there is no guarantee that the accuracy of the artificial neural network CAD engine will be improved in a re-training process.

The prior art technologies are configured to store user feedback in a database and be re-trained on the feedback without evaluating or determining the user feedback through a doctor's modification, so that re-training is performed even when re-training is not actually required, which may become a factor that degrades the accuracy of the existing artificial neural network-based CAD engine.

An object of the present invention is to propose an artificial neural network-based medical image reading and/or diagnosis assistance system in which a first artificial neural network configured to generate a first analysis result and a style learning model configured to receive and be trained on user feedback are separated from each other, thereby expecting additional performance improvement based on user feedback without directly affecting the existing performance of the first artificial neural network as a CAD engine.

Although a doctor, who is a user, has substantially approved a first analysis result, there may be a preferred styling pattern in the process of visually representing the first analysis result. For example, when the first analysis result is a vessel segmentation result, a first artificial neural network may segment and display only the inner region of the blood vessel, but a user may prefer to visualize a segmentation result including the wall of the blood vessel.

Furthermore, in the case of the breast, the first artificial neural network may segment and display only a tissue inside the skin. In this case, a user may prefer to visualize a segmentation result including even a skin tissue.

Accordingly, an object of the present invention is to propose an artificial neural network-based medical image reading and/or diagnosis assistance system in which a style learning model is trained on a styling pattern preferred by a user and provides a second analysis result reflecting a user-preferred style corresponding to a first analysis result of a first artificial neural network.

An object of the present invention is to propose an artificial neural network-based medical image reading and/or diagnosis assistance system which may be trained on a user-preferred styling pattern by means of a style learning model which is constructed and is trained independently of a first artificial neural network-based CAD engine.

An object of the present invention is to propose an artificial neural network-based medical image reading and/or diagnosis assistance system which detects user feedback for a first analysis result, determines whether to allow a style learning model to be trained on the user feedback, and allows the style learning model to be trained on user feedback determined to be trained on by the style learning model and a first analysis result corresponding to the user feedback.

An object of the present invention is to provide a criterion for determining whether to allow a style learning model to be trained on user feedback on a first analysis result.

An object of the present invention is to propose an artificial neural network-based medical image reading and/or diagnosis assistance system which evaluates whether a first analysis result is accepted by a user, who is a doctor, based on user feedback on the first analysis result and allows a style learning model to be trained on the first analysis result and the user feedback when the user accepts the first analysis result.

An object of the present invention is to propose an artificial neural network-based medical image reading and/or diagnosis assistance system which may partially use the information of the inner layer of a first artificial neural network which provides a first analysis result when generating a second analysis result reflecting a user-preferred style for the first analysis result.

An object of the present invention is to propose an artificial neural network-based medical image reading and/or diagnosis assistance system which, when generating a second analysis result reflecting a user-preferred style for the first analysis result, may receive a first medical image, i.e., the basis of a first analysis result, and may allow a style learning model to provide a detailed styling result based on the context information, such as the body part and the organ, of the first medical image. In this case, the style learning model may be trained on a detailed user-preferred style based on the context information.

According to an aspect of the present invention, there is provided an artificial neural network-based medical image reading and/or diagnosis assistance apparatus for assisting in reading and/or diagnosing a medical image based on a medical artificial neural network, the medical image reading and/or diagnosis assistance apparatus including a computing system, wherein the computing system includes at least one processor. The at least one processor is configured to acquire or receive a first analysis result obtained through the inference of a first artificial neural network about a first medical image, to detect user feedback on the first analysis result input by a user, to determine whether the first analysis result and the user feedback satisfy training conditions, and to transfer the first analysis result and the user feedback satisfying the training conditions to a style learning model so that the style learning model is trained on the first analysis result and the user feedback.

The at least one processor may be further configured to determine whether the first analysis result and the user feedback satisfy the training conditions based on at least one of the similarity between a user-modified first analysis result generated based on the user feedback on the first analysis result and the first analysis result, the size of a difference region between the first analysis result and the user-modified first analysis result, the shape of the difference region, and the distribution of the brightness values of the difference region in the first medical image.

The at least one processor may be further configured to determine the similarity between the user-modified first analysis result and the first analysis result based on at least one of the Hausdorff distance between a first set of pixels or voxels included in a first boundary of the first analysis result and a modified first set of pixels or voxels included in a user-modified first boundary of the user-modified first analysis result and the ratio between a first area or first volume of an area surrounded by the first boundary and a modified first area or modified first volume of an area surrounded by the user-modified first boundary.

The at least one processor may be further configured to evaluate whether the user accept the first analysis result based on the user feedback on the first analysis result, and to, when the user accepts the first analysis result, determine that the first analysis result and the user feedback satisfy the training conditions.

The at least one processor may be further configured to receive a prediction result predicting whether the user will accept the first analysis result, and to determine whether the first analysis result and the user feedback satisfy the training conditions based on the prediction result.

The at least one processor may be further configured to receive a preliminary first analysis result, which is an output before a final layer inside the first artificial neural network, together with the first analysis result, and to transfer the preliminary first analysis result to the style learning model together with the first analysis result and the user feedback satisfying the training conditions, and control the training of the style learning model so that the style learning model is trained on the relationships among the first analysis result, the preliminary first analysis result, and the user feedback.

The at least one processor may be further configured to controls the training of the style learning model so that the style learning model is trained on the relationship between the first analysis result and the user feedback based on context information including body part and organ information included in the first medical image.

The style learning model may be a second artificial neural network, and the computing system may further include the second artificial neural network. The at least one processor may be further configured to input the first analysis result and the user feedback satisfying the training conditions to the second artificial neural network, and to control the training of the second artificial neural network so that the second artificial neural network is trained on the relevance between the first analysis result and the user feedback satisfying the training conditions.

The computing system may further include a communication interface configured to transmit and receive data to and from the first artificial neural network outside the computing system. The at least one processor may be further configured to acquire and receive the first analysis result obtained through the inference of the first artificial neural network about the first medical image via the communication interface.

The at least one processor may be further configured to provide a first user menu configured to receive information about whether the user has approved the first analysis result for the first medical image, and to, when the user has approved the first analysis result via the first user menu, determine that the first analysis result and the user feedback satisfy the training conditions.

According to another aspect of the present invention, there is provided an artificial neural network-based medical image reading and/or diagnosis assistance apparatus for assisting in diagnosing a medical image based on a medical artificial neural network, the medical image reading and/or diagnosis assistance apparatus including a computing system, wherein the computing system includes at least one processor. The at least one processor is configured to acquire or receive a first analysis result obtained through the inference of a first artificial neural network about a first medical image, to control a style learning model so that the style learning model generates a second analysis result for the first analysis result, and to visualize the first medical image and the second analysis result together and provide the visualized first medical image and second analysis result to a user.

The at least one processor may be further configured to verify whether the second analysis result is valid as an analysis result for the first medical image based on the result of the comparison between the first analysis result and the second analysis result.

The at least one processor may be further configured to verify whether the second analysis result is valid as an analysis result for the first medical image based on at least one of the similarity between the first analysis result and the second analysis result, the size of a difference region between the first analysis result and the second analysis result, the shape of the difference region, and the distribution of the brightness values of the difference region in the first medical image.

The at least one processor may be further configured to visualize the first medical image, the first analysis result, and the second analysis result so that the first analysis result and the second analysis result are compared in association with the first medical image, and to provide the visualized first medical image, first analysis result and second analysis result to the user.

The at least one processor may be further configured to receive a preliminary first analysis result, which is an output before a final layer inside the first artificial neural network, together with the first analysis result, to transfer the first medical image and the preliminary first analysis result to the style learning model together with the first analysis result, and to control the inference of the style learning model so that the style learning model generates the second analysis result based on an inference process using the first analysis result, the preliminary first analysis result, and the first medical image as inputs.

The at least one processor may be further configured to transfer the first medical image together with the first analysis result to the style learning model, and to control the inference of the style learning model so that the style learning model performs an inference process using the first analysis result and the first medical image as inputs to generate the second analysis result based on context information including body part and organ information included in the first medical image.

According to still another aspect of the present invention, there is provided an artificial neural network-based medical image reading and/or diagnosis assistance method that is performed by a computing system, wherein the computing system includes at least one processor. The artificial neural network-based medical image reading and/or diagnosis assistance method includes: acquiring or receiving, by the at least one processor, a first analysis result obtained through the inference of a first artificial neural network about a first medical image; detecting, by the at least one processor, user feedback on the first analysis result input by a user; determining, by the at least one processor, whether the first analysis result and the user feedback satisfy training conditions; and transferring, by the at least one processor, the first analysis result and the user feedback satisfying the training conditions to a style learning model so that the style learning model is trained on the first analysis result and the user feedback.

According to still another aspect of the present invention, there is provided an artificial neural network-based medical image reading and/or diagnosis assistance method that is performed by a computing system, wherein the computing system includes at least one processor. The artificial neural network-based medical image reading and/or diagnosis assistance method includes: acquiring or receiving, by the at least one processor, a first analysis result obtained through the inference of a first artificial neural network about a first medical image; controlling, by the at least one processor, a style learning model so that the style learning model generates a second analysis result for the first analysis result; and visualizing, by the at least one processor, the first medical image and the second analysis result together, and providing, by the at least one processor, the visualized first medical image and second analysis result to a user.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Other objects and features of the present invention in addition to the above-described objects will be apparent from the following description of embodiments taken with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Deep learning/CNN-based artificial neural network technology, which has recently developed rapidly, is considered for the purpose of identifying a visual element that is difficult to identify with the human eye when it is applied to the imaging field. The field of application of the above technology is expected to expand to various fields such as security, medical imaging, and non-destructive testing.

For example, in the medical imaging field, there are cases where a tissue in question is not immediately diagnosed as a cancer tissue in a biopsy state but whether it is a cancer tissue is determined only after being monitored from a pathological point of view. Although it is difficult to determine whether a corresponding cell is a cancer tissue in a medical image with the human eye, there is an expectation that the application of artificial neural network technology may acquire more accurate prediction results than observation with the human eye.

It is expected that this artificial neural network technology is applied and performs the analysis process of detecting a disease or lesion difficult to identify with the human eye in a medical image, segmenting a region of interest such as a specific tissue, and measuring the segmented region.

The present invention is directed to a medical image reading and/or diagnosis assistance system that provides a configuration that visualizes various analysis techniques, to which such artificial neural network technology is applied, in the most appropriate form that can be diagnosed by human professions.

Figure 1:
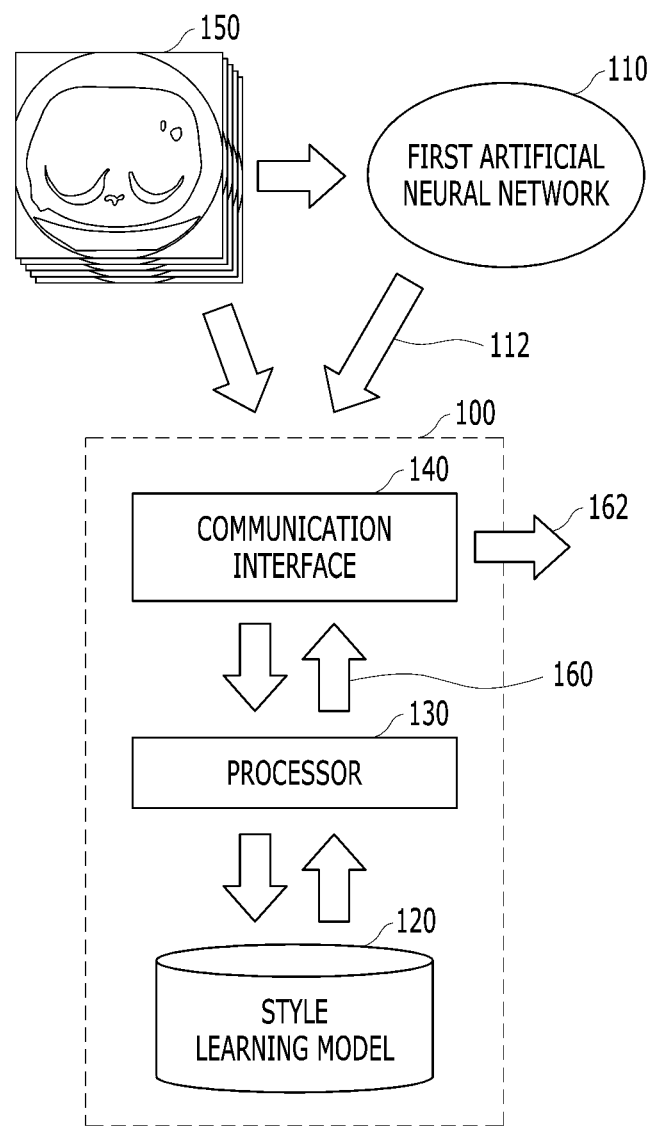
FIG. 1 is a diagram showing a medical image reading and/or diagnosis assistance apparatus that provides styling based on a user-preferred style based on a medical artificial neural network according to an embodiment of the present invention.

FIG. 1 is a diagram showing a medical image reading and/or diagnosis assistance apparatus that provides styling based on a user-preferred style based on the analysis result of a medical artificial neural network according to an embodiment of the present invention.

Referring to FIG. 1, the medical image reading and/or diagnosis assistance apparatus according to the present embodiment includes a computing system 100, and the computing system 100 includes at least one processor 130. The computing system 100 may further include a style learning model 120. The at least one processor 130 acquires or receives a first analysis result 112 obtained by the inference of a first artificial neural network 110 about a first medical image 150, generates a second analysis result 160 reflecting a user-preferred style based on the first analysis result 112 in cooperation with the style learning model 120, and generates visualization information 162 that allows the first medical image 150 and the second analysis result 160 to be displayed on a screen. The at least one processor 130 may control the style learning model 120 so that the style learning model 120 generates the second analysis result 160 reflecting a user-preferred style for the first analysis result 112.

Although a doctor, who is a user, has substantially approved the first analysis result 112, there may be a preferred styling pattern in the process of visually representing the first analysis result 112. For example, when the first analysis result 112 is a vessel segmentation result, the first artificial neural network 110 may segment and display only the inner region of the blood vessel, but the user may prefer to visualize a segmentation result including the wall of the blood vessel.

Furthermore, in the case of the breast, the first artificial neural network 110 may segment and display only a tissue inside the skin. In this case, a user may prefer to visualize a segmentation result including even a skin tissue.

The style learning model 120 may be trained on a styling pattern preferred by a user so that the style learning model 120 inside the computing system 100 of the medical image reading and/or diagnosis assistance apparatus according to the present embodiment provides the second analysis result 160 in which the first analysis result 112 is modified by reflecting a user-preferred style.

In the medical image reading and/or diagnosis assistance apparatus according to the present embodiment, the first artificial neural network 110 configured to generate the first analysis result 112 and the style learning model 120 configured to receive and be trained by user feedback are separated from each other. The style learning model 120 may be configured and trained independently of the first artificial neural network 110. The training process and training result of the style learning model 120 do not directly affect the performance of the first artificial neural network 110. It is obvious that the training process and training result of the style learning model 120 may be used as reference data for the retraining of the first artificial neural network 110 in the future. After the first artificial neural network 110 has undergone retraining, it will have completely different performance from that of the first artificial neural network 110 described in the present invention. Accordingly, the retraining of the first artificial neural network 110 is not further described therein.

The first artificial neural network 110 is an artificial neural network that has received a predetermined training medical image set and has been trained to perform analysis on a medical image. After training has been completed, the first artificial neural network 110 is installed at a medical site, and may cooperate with the computing system 100 of the present invention in an offline state at the medical site. The style learning model 120 may be trained on a user-preferred style in an online state at the medical site. The style learning model 120 does not affect the analysis performance of the first artificial neural network 110, and is trained on a user-preferred style and generates the second analysis result 160 in which the user-preferred style has been reflected in the first analysis result 112 of the first artificial neural network 110.

The at least one processor 130 may detect user feedback on the first analysis result 112, and may control the style learning model 120 so that the style learning model 120 can be trained on the user feedback.

The at least one processor 130 may determine whether to allow the style learning model 120 to be trained on the user feedback on the first analysis result 112. The at least one processor 130 may determine whether the first analysis result 112 and the user feedback satisfy training conditions.

The at least one processor 130 may transfer the first analysis result 112 and user feedback satisfying the training conditions, i.e., the user feedback classified such that the style learning model 120 is trained thereon and the first analysis result 112 corresponding thereto, to the style learning model 120 so that the style learning model 120 can be trained thereon.

The medical image reading and/or diagnosis assistance apparatus according to the present embodiment may present a criterion for determining whether to allow the style learning model 120 to be trained on the user feedback on the first analysis result 112.

The at least one processor 130 may determine whether the first analysis result 112 and the user feedback satisfy the training conditions based on at least one of: the similarity between a user-modified first analysis result generated based on the user feedback on the first analysis result 112 and the first analysis result 112; the size of a difference region between the first analysis result 112 and the user-modified first analysis result; the shape of the difference region; and the distribution of the brightness values of the difference region in the first medical image 150.

For example, when the first analysis result 112 is a vessel segmentation result, the similarity between the user-modified vessel segmentation result and the first analysis result 112 may be calculated based on pixels or voxels. The at least one processor 130 may determine the similarity between the user-modified first analysis result and the first analysis result 112 based on at least one of: the Hausdorff distance between a first set of pixels or voxels included in the first boundary of the first analysis result 112 and a modified first set of pixels or voxels included in the user-modified first boundary of the user-modified first analysis result; and the ratio between the first area or first volume of the area surrounded by the first boundary and the modified first area or modified first volume of the area surrounded by the user-modified first boundary.

A difference region between the user-modified vessel segmentation result and the first analysis result 112 may be calculated, and it may be determined based on the shape of the difference region and/or the size of the difference region whether the user feedback on the first analysis result 112 indicates that the first analysis result 112 has been accepted by a user who is a doctor. Since the at least one processor 130 may receive not only the first analysis result 112 but also the first medical image 150, an anatomical feature indicated by the difference region may be extracted based on the distribution of the brightness values of the difference region in the first medical image 150. For example, there is assumed a case where an object in question is determined to correspond to a vessel wall based on the facts that the difference region between the user vessel segmentation result and the first analysis result 112 is considerably narrow and long, the area or volume of the object is small compared to the length thereof, and the distribution of the brightness values of the object in the first medical image 150 corresponds to that of the vessel wall. In this case, the at least one processor 130 may determine that a user has actually accepted the first analysis result 112 and has made a modification such that only the vessel wall is included in or excluded from the first analysis result 112. This may be viewed as a case where a user-preferred style for the first analysis result 112 is apparently present. Accordingly, the at least one processor 130 may transmit the user feedback and the first analysis result 112 corresponding to the user feedback to the style learning model 120, and may control the style learning model 120 so that the style learning model 120 is trained on the relationship between the first analysis result 112 and the user feedback. In this case, the style learning model 120 may be trained on the relationship between the first analysis result 112 and the user feedback or the relationship between the first analysis result 112 and the user-modified analysis result.

The at least one processor 130 may evaluate whether the user has accepted the first analysis result 112 based on the user feedback on the first analysis result 112, and may determine that the first analysis result 112 and the user feedback satisfy the training conditions when the user has accepted the first analysis result 112. When the user has accepted the first analysis result 112, the at least one processor 130 may control the style learning model 120 so that the style learning model 120 is trained on the first analysis result 112 and the user feedback. In other words, when the user feedback is detected and it is determined based on the analysis of the user feedback that the user's intention is to generally accept the first analysis result 112 and want a minor style change to the first analysis result 112, the style learning model 120 may be trained on the user feedback and the first analysis result 112.

In the medical image reading and/or diagnosis assistance apparatus according to the present embodiment, a separate evaluation artificial neural network (not shown) configured to evaluate whether the user accept the first analysis result 112 may be included. The evaluation artificial neural network may be included in the computing system 100, and may be trained and infer independently of the first artificial neural network 110. The evaluation artificial neural network may receive a training analysis result provided by the first artificial neural network 110, may receive a user evaluation result for the training analysis result, and may be trained on the relationship between the training analysis result and the user evaluation result. In this case, the user evaluation result may include approval for or rejection of the training analysis result. When the at least one processor 130 transmits the first analysis result 112 of the first artificial neural network 110 to the evaluation artificial neural network, the evaluation artificial neural network may predict a user evaluation result for the first analysis result 112 through inference about the first analysis result 112. For example, the evaluation artificial neural network may predict that the user will approve or reject the first analysis result 112. In this case, the evaluation artificial neural network is trained and infers independently of the first artificial neural network 110, and thus the training and inference of the evaluation artificial neural network do not directly affect the performance of the first artificial neural network 110. However, this may become a means for supporting the retraining of the first artificial neural network 110 by feeding back the inference of the evaluation artificial neural network to the first artificial neural network 110 in the future.

The at least one processor 130 receives a prediction result predicting whether the user will accept the first analysis result 112 from the evaluation artificial neural network, and may determine whether the first analysis result 112 and the user feedback satisfy the training conditions based on the prediction result of the evaluation artificial neural network.

The at least one processor 130 may receive a preliminary first analysis result (not shown), which is an output before a final layer inside the first artificial neural network 110, together with the first analysis result 112, may transmit the preliminary first analysis result (not shown) to the style learning model 120 together with the first analysis result 112 and the user feedback satisfying the training conditions, and may control the training of the style learning model 120 so that the style learning model 120 can be trained on the relationships among the first analysis result 112, the preliminary first analysis result (not shown), and the user feedback.

For the user feedback determined to be trained on by the style learning model 120, the at least one processor 130 may additionally receive the output of the first analysis result 112 corresponding to the user feedback before the final layer inside the first artificial neural network 110, and may transmit the output to the style learning model 120 together with the first analysis result 112, the first medical image 150, and the user feedback. The style learning model 120 may receive all information before and after the final layer the shape of which is determined by the first artificial neural network 110, and may perform the role of the final layer the shape of which is determined by the first artificial neural network 110 instead. Furthermore, it may be understood that the style learning model 120 receives not only the first analysis result 112 of the first artificial neural network 110 but also the information held inside the first artificial neural network 110 beforehand and is used in the process of being trained on the user-preferred style.

The at least one processor 130 may control the training of the style learning model 120 so that the style learning model 120 can be trained on the relationship between the first analysis result 112 and the user feedback based on the context information including body part and organ information included in the first medical image.

The computing system 100 may further include a communication interface 140 configured to transmit and receive data to and from the external first artificial neural network 110. The at least one processor 130 may obtain or receive the first analysis result 112 obtained by the inference of the first artificial neural network 110 about the first medical image 150 via the communication interface 140.

The at least one processor 130 may provide a first user menu configured to receive information about whether the user has approved the first analysis result 112 of the first medical image 150, and may determine that the first analysis result 112 and the user feedback satisfy the training conditions when the user has approved the first analysis result 112 via the first user menu. According to an embodiment of the present invention, a user menu may be configured such that information about whether the user has approved the first analysis result 112 is included in the user feedback. In this case, a user interface (UI) may be configured such that the user approves the first analysis result 112 first and then modifies the first analysis result 112 according to a user-preferred style. Since the user has approved the first analysis result 112, it may be assumed that later user feedback corresponds to the user-preferred style. Under the control of the at least one processor 130, the style learning model 120 may extract and be trained on a pattern of user-preferred styles.

The style learning model 120 having learned the user-preferred style may generate the second analysis result 160 reflecting the user-preferred style for the first analysis result 112 under the control of the at least one processor 130.

There may be added the process of verifying whether the second analysis result 160 provided by the style learning model 120 is valid as a modification of the styling pattern without significantly deviating from the first analysis result 112. The at least one processor 130 may verify whether the second analysis result 160 is valid as an analysis result for the first medical image 150 based on the result of the comparison between the first analysis result 112 and the second analysis result 160. The at least one processor 130 may verify whether the second analysis result 160 is valid as an analysis result for the first medical image 150 based on at least one of: the similarity between the first analysis result 112 and the second analysis result 160; the size of the difference region between the first analysis result 112 and the second analysis result 160; the shape of the difference region; and the distribution of the brightness values of the difference region in the first medical image 150.

The at least one processor 130 may visualize the first analysis result 112 and the second analysis result 160 so that the first analysis result 112 and the second analysis result 160 can be compared in association with the first medical image 150, and may provide the visualized first and second analysis results 112 and 160 to the user. In this case, the second analysis result 160 obtained by the inference of the style learning model 120 based on the training on the user-preferred style may be provided together with the first analysis result 112, and then the user may select one of the first analysis result 112 and the second analysis results 160. When the user approves the second analysis result 160, it may be understood that this is an approval for the first analysis result 112 and also the second analysis result 160 has passed through the verification of whether the second analysis result 160 appropriately reflects the user-preferred style. In other words, it can be understood that both the process of approving the first analysis result 112 and the process of verifying whether the second analysis result 160 is a valid styling modification are replaced by the user's approval.

The medical image reading and/or diagnosis assistance apparatus according to the present embodiment may partially use the information of the inner layer of the first artificial neural network 110 providing the first analysis result 112 when generating the second analysis result 160 reflecting the user-preferred style for the first analysis result 112. The at least one processor 130 may receive a preliminary first analysis result (not shown), which is an output before a final layer inside the first artificial neural network 110, together with the first analysis result 112, may transmit the first medical image 150 and the preliminary first analysis result to the style learning model 120 together with the first analysis result 112, and may control the inference of the style learning model 120 so that the style learning model 120 generates the second analysis result 160 based on an inference process using the first analysis result 112, the preliminary first analysis result, and the first medical image 150 as inputs.

The at least one processor 130 may transmit the first medical image 150 together with the first analysis result 112 to the style learning model 120, and may control the inference of the style learning model 120 so that the style learning model 120 performs an inference process using the first analysis result 112 and the first medical image 150 as inputs, i.e., the style learning model 120 generates the second analysis result 160 based on context information including body part and organ information.

When generating the second analysis result 160 reflecting the user-preferred style for the first analysis result 112, the medical image reading and/or diagnosis assistance apparatus according to the present embodiment may receive the first medical image 150, which is the basis of the first analysis result 112, and the style learning model 120 may provide a detailed styling result based on the context information, such as body part and organ information, of the first medical image 150. In this case, the style learning model 120 may be trained on a detailed user-preferred style based on the context information.

The second analysis result 160 reflecting the user-preferred style may be generated in a form most appropriate to assist in reading and/or diagnosing the first medical image 150. The second analysis result 160 may be derived in a form suitable for a medical professional, i.e., user, to determine the first analysis result 112 or to make a decision on the first analysis result 112.

The second analysis result 160 of a type suitable based on the type of first analysis result 112, the analysis content included in the first analysis result 112, and/or the type of disease or lesion to be diagnosed by the first analysis result 112 may be extracted and trained in advance by the style learning model 120. In this case, after receiving the first analysis result 112, the processor 130 may request the second analysis result 160 from the style learning model 120 based on the analysis content included in the first analysis result 112 and the content of the first medical image 150 with which the first analysis result 112 is associated, and the style learning model 120 may transmit the first analysis result 112 and the second analysis result 160 corresponding to the first medical image 150 to the processor 130 in response to a request from the processor 130. The processor 130 may transmit the second analysis result 160, received from the style learning model 120, to the communication interface 140. Although the learning and training process of the style learning model 120 may be implemented using an artificial neural network, the spirit of the present invention is not limited thereto, and may be performed in a rule-based manner in some cases.

The at least one processor 130 may provide a first user menu configured to receive a user approval for the second analysis result 160 displayed on the screen together with the first medical image 150. The first user menu may be provided as a user interface configured to allow a user to select either "confirm" or "reject." Furthermore, the at least one processor 130 may display the first analysis result 112 on the screen so that the first analysis result 112 can be compared with the second analysis result 160, and may implement a first user menu configured to receive a user approval for each or all of them.

When the user approves both the first analysis result 112 and the second analysis result 160, it may be considered that a user approves the inference result of the first artificial neural network 110 and also approves the fact that the second analysis result 160 is a valid styling modification result reflecting the user-preferred style. When the user approves the first analysis result 112 and rejects the second analysis result 160, it may be considered that the user approves the inference result of the first artificial neural network 110, but the user-preferred style has not been appropriately reflected or there is no need to reflect the user-preferred style.

When the user does not approve the second analysis result 160, the at least one processor 130 may provide a second user menu configured to generate a third analysis result corresponding to the second analysis result 160 for the first medical image 150 independently of the second analysis result 160. The second user menu may be a menu configured to generate a third analysis result that replaces the second analysis result 160. The second user menu may be a menu configured to manually or semi-automatically generate the third analysis result, and may be partially automatically executed, intermittently receive a user input in an interactive manner, generate a third analysis result, and replace the second analysis result 160 with the third analysis result.

In FIG. 1, there is shown the embodiment in which the first artificial neural network 110 is located outside the computing system 100. The process of connecting to a location outside the computing system 100 is performed via the communication interface 140. Accordingly, the processor 130 may receive the first analysis result 112, generated by the first artificial neural network 110, via the communication interface 140, and may receive or acquire the first medical image 150 via the communication interface 140. The second analysis result 160 generated through the cooperation between the processor 130 and the style learning model 120 may be combined with the first medical image 150 and/or the first analysis result 112 and generated as the visualization information 162, and may be transferred to a display (not shown) outside the computing system 100 via the communication interface 140. The process of generating the visualization information 162 based on the second analysis result 160 may be performed by the processor 130, or may be performed by the communication interface 140 under the control of the processor 130.

Depending on the type of first analysis result 112, the at least one processor 130 may generate the visualization information 162 by overlaying the first analysis result 112 and/or the second analysis result 160 on the first medical image 150 and provide visualization. For example, when the first analysis result 112 is an analysis result related to the detection of a lesion or diagnosis of a lesion, the first analysis result 112 and/or the second analysis result 160 may be overlaid on the first medical image 150.

According to another embodiment of the present invention, the visualization information 162 includes the result of the reconstruction or reformatting of the first medical image 150. Depending on the type of first analysis result 112, the visualization information 162 may be generated such that the first analysis result 112 and/or the second analysis result 160 are included in the visualization information 162 together with the result of the reconstruction or reformatting of the first medical image 150. When the visualization information 162 includes the result of the reconstruction or reformatting of the first medical image 150, the at least one processor 130 may be involved in the generation of the visualization information 162.

The first artificial neural network 110 may provide at least one of image segmentation, lesion detection and clinical diagnosis results for the first medical image 150 as the first analysis result 112. It is highly likely that a user-preferred style is reflected in the visualization of a boundary included in the image segmentation result, the lesion detection result, or the like. To clinically assist the facilitation of image diagnosis, a user-preferred style modification pattern regarding whether the image segmentation result, the lesion detection result, or the like further includes information about the surroundings of an anatomical structure or includes only a segmented or detected region may be tracked and trained on online. As a result, it may be possible to derive the second analysis result 160 that visualizes the first analysis result 112 in the user-preferred style without affecting the first artificial neural network 110. The user feedback on the second analysis result 160 itself may be reused for the training of the style learning model 120.

The first artificial neural network 110 may be an artificial neural network that receives information in which a professional diagnoses a plurality of types of diseases for a single body part included in a plurality of respective training medical images and is trained on the function of diagnosing the plurality of types of diseases included in the plurality of respective training medical images. In this case, the first artificial neural network 110 may be a case of having been trained on the function of diagnosing a plurality of types of diseases using a neural network model.

Figure 2:
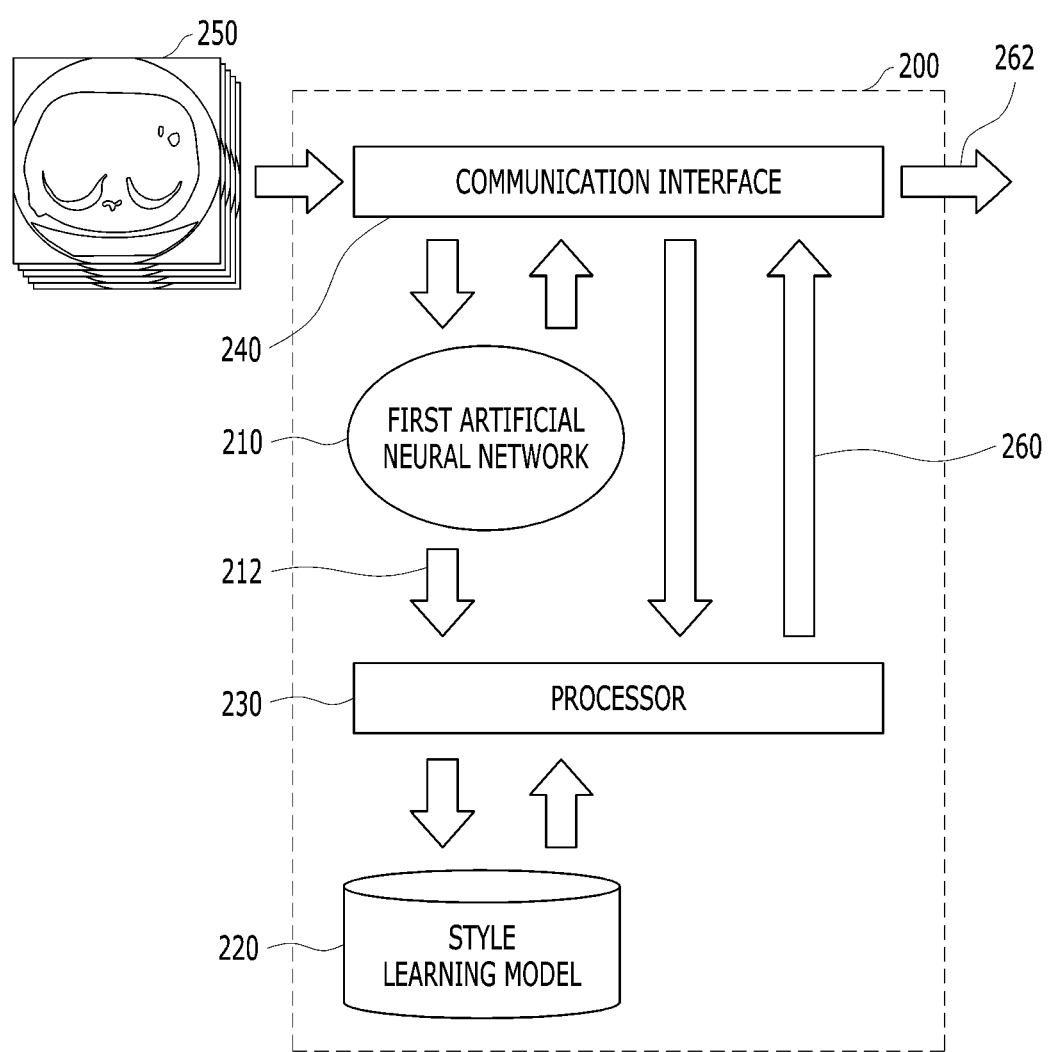
FIG. 2 is a diagram showing a medical image reading and/or diagnosis assistance apparatus that provides styling based on a user-preferred style based on a medical artificial neural network according to an embodiment of the present invention.

FIG. 2 is a diagram showing a medical image reading and/or diagnosis assistance apparatus that provides styling based on a user-preferred style based on the analysis result of a medical artificial neural network according to an embodiment of the present invention.

Referring to FIG. 2, the medical image reading and/or diagnosis assistance apparatus according to the present embodiment includes a computing system 200, and the computing system 200 includes at least one processor 230. The computing system 200 may further include a style learning model 220. The at least one processor 230 acquires or receives a first analysis result 212 obtained through the inference of a first artificial neural network 210 about a first medical image 250, generates a second analysis result 260 reflecting a user-preferred style for the first medical image 250 based on the first analysis result 212 in cooperation with the style learning model 220, and generates visualization information 262 that allows the first medical image 250 and the second analysis result 260 to be displayed on a screen.

In FIG. 2, there is shown the embodiment in which the first artificial neural network 210 is included in the computing system 200. A communication interface 240 may acquire or receive the first medical image 250 from the outside. The communication interface 240 may transmit the first medical image 250 to the first artificial neural network 210 under the control of the processor 230, and may transmit the first medical image 250 to the processor 230.

The first artificial neural network 210 may generate the first analysis result 212 for the first medical image 250 under the control of the processor 230, and may transfer the first analysis result 212 to the processor 230 under the control of the processor 230.

The processor 230 may generate a second analysis result 260 based on the first analysis result 212 and the first medical image 250, and may transmit the second analysis result 260 to the communication interface 240.

Since the other operations of the processor 230, the communication interface 240, the first artificial neural network 210, and the style learning model 220 are the same as those of the processor 130, communication interface 140, first artificial neural network 110, and style learning model 120 of FIG. 1, redundant descriptions thereof will be omitted.

Figure 3:
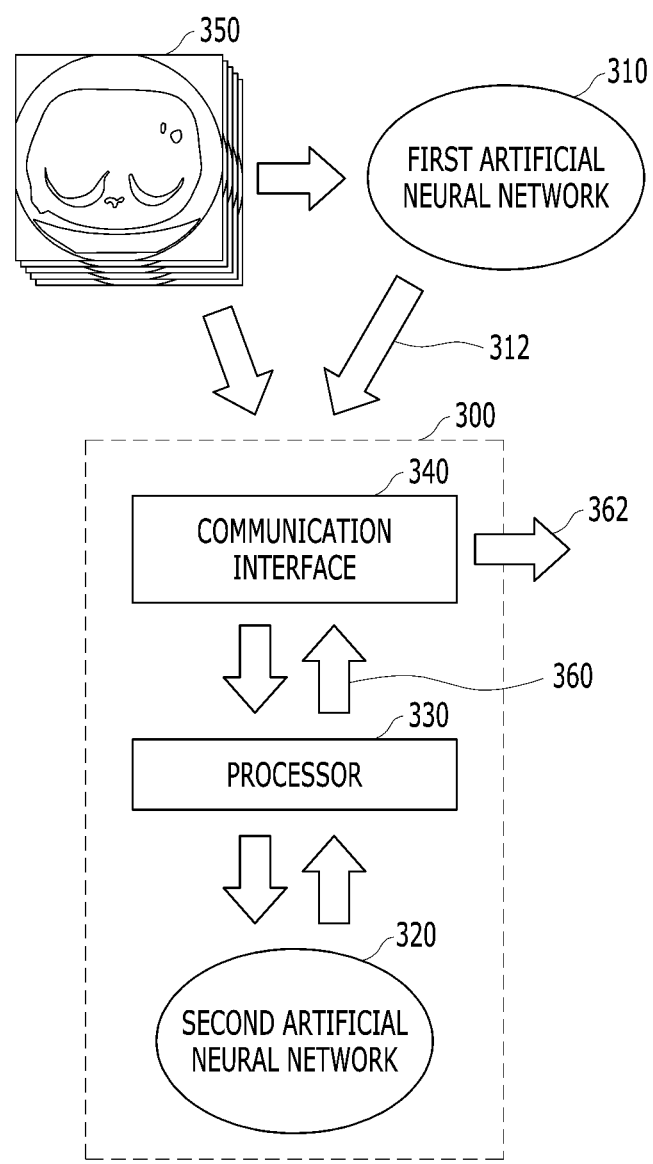
FIG. 3 is a diagram showing a medical image reading and/or diagnosis assistance apparatus that provides styling based on a user-preferred style based on a medical artificial neural network according to an embodiment of the present invention.

FIG. 3 is a diagram showing a medical image reading and/or diagnosis assistance apparatus that provides styling based on a user-preferred style based on the analysis result of a medical artificial neural network according to an embodiment of the present invention.

Referring to FIG. 3, the medical image reading and/or diagnosis assistance apparatus according to the present embodiment includes a computing system 300, and the computing system 300 includes at least one processor 330.

In the embodiment of FIG. 3, the style learning model 120 or 220 of FIG. 1 or 2 is replaced with a second artificial neural network 320. The computing system 300 may further include the second artificial neural network 320. The at least one processor 330 acquires or receives a first analysis result 312 obtained through the inference of the first artificial neural network 310 about the first medical image 350, generates a second analysis result 360 reflecting a user-preferred style for the first medical image 350 through the inference of the second artificial neural network 320 by providing the first analysis result 312 as an input of the second artificial neural network 320, and generates visualization information 362 that allows the first medical image 350 and the second analysis result 360 to be displayed on a screen based on the second analysis result 360.

The at least one processor 130 may input the first analysis result 312 and user feedback, satisfying training conditions, to the second artificial neural network 320, and may control the training of the second artificial neural network 320 so that the second artificial neural network 320 is trained on the relationship between the first analysis result 112 and the user feedback that satisfy the training conditions.

The second artificial neural network 320 may be an artificial neural network that has received a plurality of user feedbacks in which a professional has modified a plurality of fourth analysis results obtained for a plurality of respective second medical images, which are other training images and has been trained on the function of generating a user-preferred style based on the relationship between the plurality of fourth analysis results and the plurality of user feedbacks in advance. The at least one processor 330 may input the first analysis result 312 to the second artificial neural network 320, and may control the artificial neural network 320 so that the second analysis result 360 is obtained through the inference of the second artificial neural network 320. When the user feedback on the second analysis result 360 is a valid styling modification (when the training conditions are satisfied), the training of the second artificial neural network 320 on the user-preferred style may be performed on the first analysis result 312 and the user feedback again, and the function may be further enhanced by this training. The first artificial neural network 310 may be a segmentation engine configured to perform image segmentation, and the second artificial neural network 320 may be a style engine configured to be trained on the user-preferred style. Alternatively, the first artificial neural network 310 may be a detection engine configured to perform lesion detection, and the second artificial neural network 320 may be a style engine configured to be trained on the user preference style.

According to a modified embodiment of the present invention, the processor 330 may receive an output result obtained through the inference of the second artificial neural network 320, and may generate a second analysis result 360 based on the output result obtained through the inference of the second artificial neural network 320. In this case, the processor 330 may generate the second analysis result 360 based on the output result obtained through the inference of the second artificial neural network 320 and context information derived for the first medical image 350.

Since the other operations of the processor 330, the communication interface 340, and the first artificial neural network 310 are the same as those of the processor 130, communication interface 140, and first artificial neural network 110 of FIG. 1, redundant descriptions thereof will be omitted.

Figure 4:
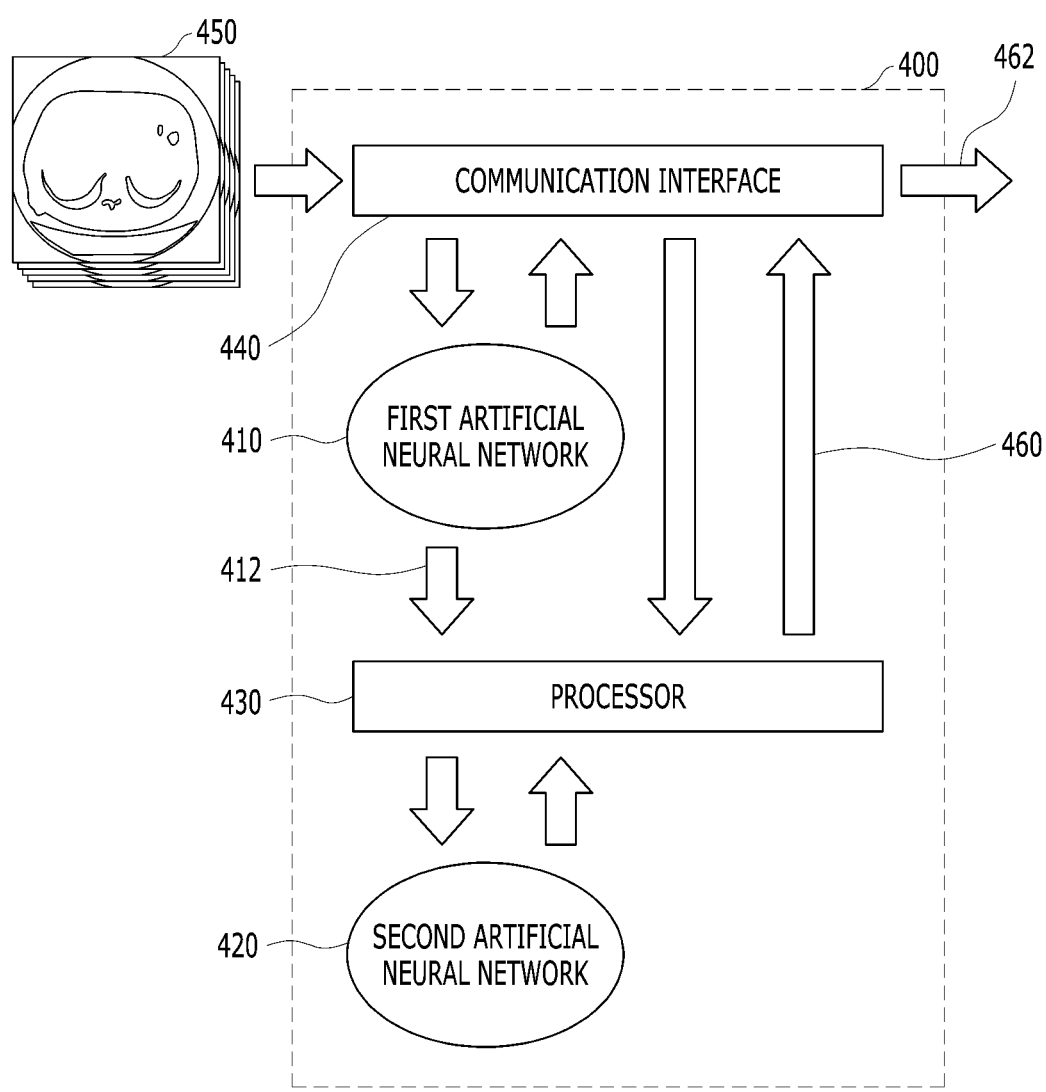
FIG. 4 is a diagram showing a medical image reading and/or diagnosis assistance apparatus that provides styling based on a user-preferred style based on a medical artificial neural network according to an embodiment of the present invention.

FIG. 4 is a diagram showing a medical image reading and/or diagnosis assistance apparatus that provides styling based on a user-preferred style based on the analysis result of a medical artificial neural network according to an embodiment of the present invention.

Referring to FIG. 4, the medical image reading and/or diagnosis assistance apparatus according to the present embodiment includes a computing system 400, and the computing system 400 includes at least one processor 430.

In FIG. 4, there is shown the embodiment in which a first artificial neural network 410 and a second artificial neural network 420 are included in the computing system 400. The at least one processor 430 acquires or receives a first analysis result 412 obtained through the inference of the first artificial neural network 410 about a first medical image 450, generates a second analysis result 460 reflecting a user-preferred style for the first medical image 450 through the inference of the second artificial neural network 420 by providing the first analysis result 412 as the input of the second artificial neural network 420, and generates visualization information 462 that allows the first medical image 450 and the second analysis result 460 to be displayed on a screen based on the second analysis result 460.

Since the other operations of the processor 430, the communication interface 440, the first artificial neural network 410, and the second artificial neural network 420 are the same as those of the processor 330, communication interface 340, first artificial neural network 310, and second artificial neural network 320 of FIG. 3, redundant descriptions thereof will be omitted.

Figure 5:
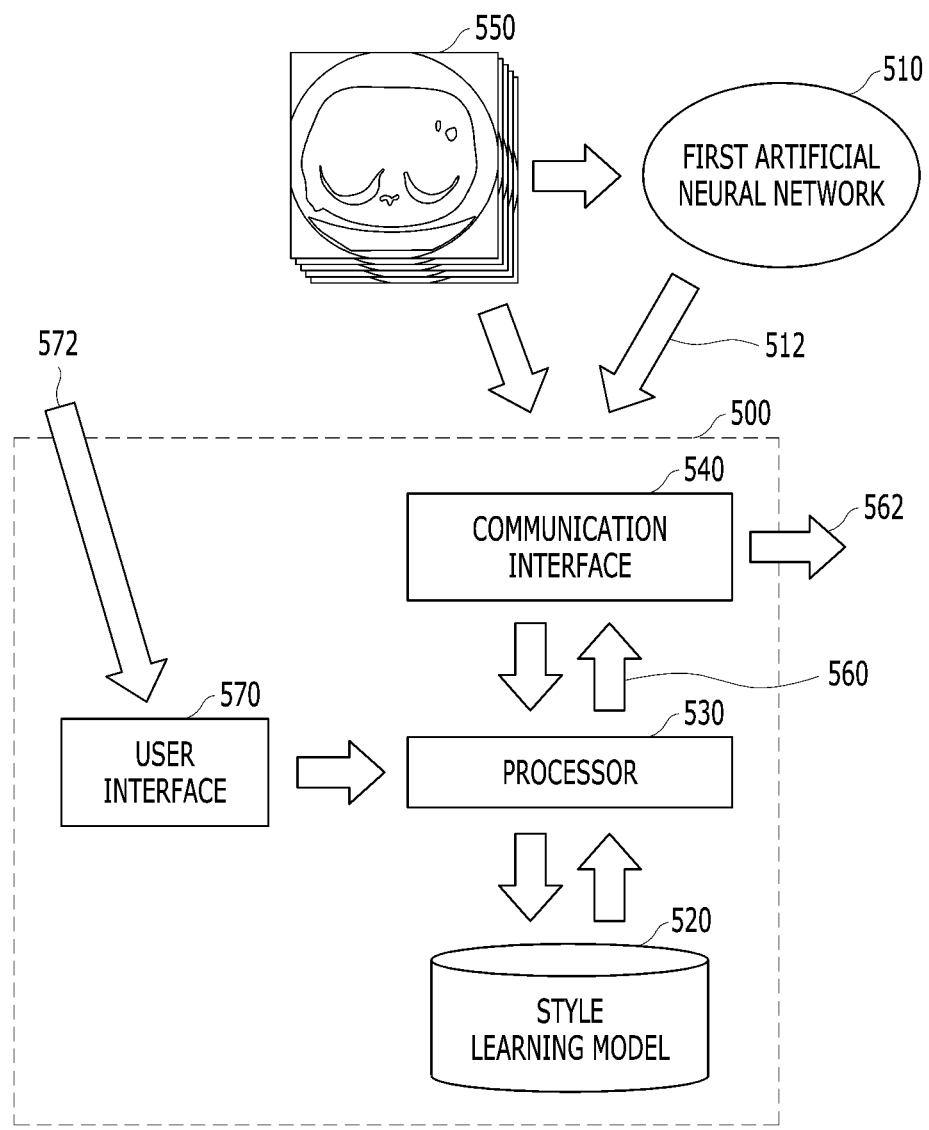
FIG. 5 is a diagram showing a medical image reading and/or diagnosis assistance apparatus that provides styling based on a user-preferred style based on a medical artificial neural network according to an embodiment of the present invention.

FIG. 5 is a diagram showing a medical image reading and/or diagnosis assistance apparatus that provides styling based on a user-preferred style based on the analysis result of a medical artificial neural network according to an embodiment of the present invention.

Referring to FIG. 5, the medical image reading and/or diagnosis assistance apparatus according to the present embodiment includes a computing system 500, and the computing system 500 includes at least one processor 530.

The computing system 500 may further include a style learning model 520. The at least one processor 530 acquires or receives a first analysis result 512 obtained through the inference of a first artificial neural network 510 about a first medical image 550, generates a second analysis result 560 reflecting a user-preferred style for the first medical image 550 based on the first analysis result 512 in cooperation with the style learning model 520, and generates visualization information 562 that allows the first medical image 550 and the second analysis result 560 to be displayed on a screen based on the second analysis result 560.

In FIG. 5, there is shown the embodiment in which the computing system 500 further includes a user interface 570 configured to receive a user input 572.

The at least one processor 530 may provide a first user menu configured to receive information about whether a user approves the first analysis result 512 displayed on the screen based on the second analysis result 560 and/or the second analysis result 560 together with the visualization information 562 to the display screen via the user interface 570. The first user menu may be a user menu configured to allow the user to select either "confirm" or "reject." According to another embodiment of the present invention, the first user menu may be provided as a visual, auditory, or tactile means, or a combination thereof.

The user interface 570 receives the user input 572, and transmits the user input 572 to the processor 530. When it is determined through the interpretation of the user input 572 that a user has not approved the second analysis result 560, the at least one processor 530 may provide a second user menu configured to generate a third analysis result corresponding to the second analysis result 560 for the first medical image 550 independently of the second analysis result 560 by using a display screen or an additional user interface menu via the user interface 570 and/or the communication interface 540. The second user menu may be an interface menu configured to generate a third analysis result replacing the second analysis result 560. The second user menu may be an interface menu configured to manually or semi-automatically generate the third analysis result. Furthermore, the second user menu may be a user menu configured to be partially automatically performed, to intermittently receive a user input in an interactive manner, to generate the third analysis result, and to replace the second analysis result 560.

Since the other operations of the processor 530, the communication interface 540, the first artificial neural network 510, and the style learning model 520 are the same as those of the processor 130, communication interface 140, first artificial neural network 110, and style learning model 120 of FIG. 1, redundant descriptions thereof will be omitted.

Figure 6:
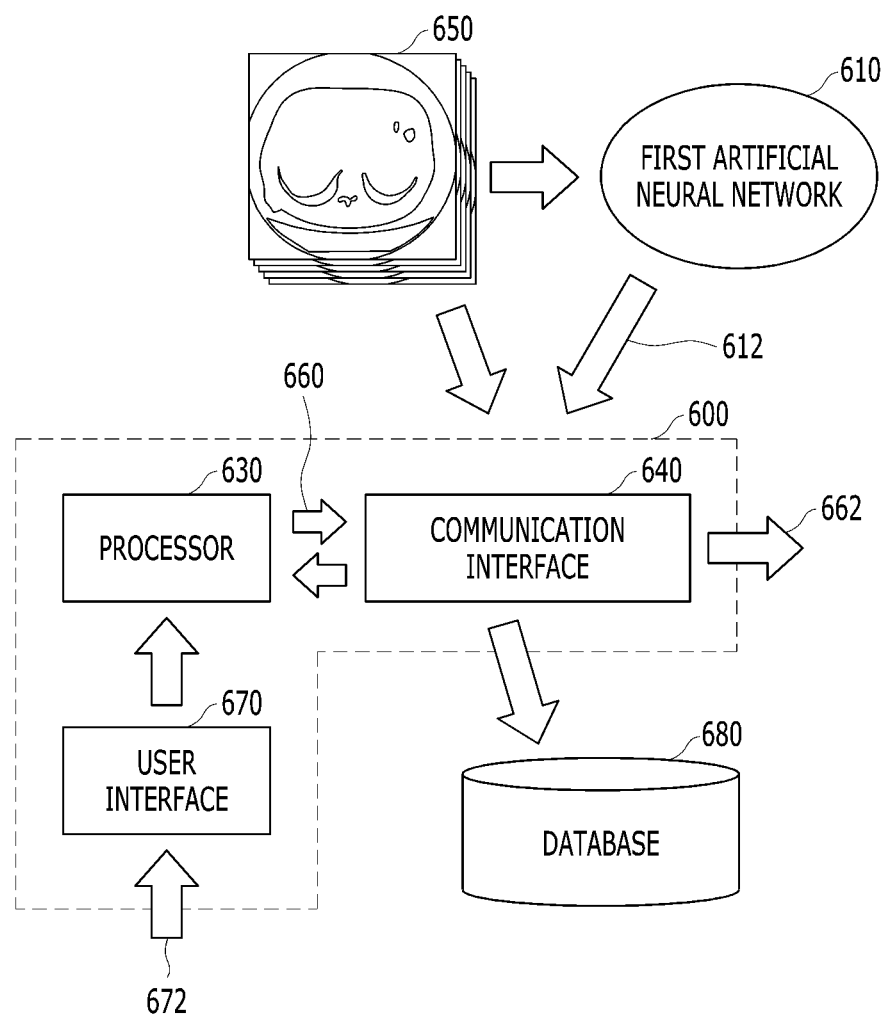
FIG. 6 is a diagram showing a medical image reading and/or diagnosis assistance apparatus that provides styling based on a user-preferred style based on a medical artificial neural network according to an embodiment of the present invention.

FIG. 6 is a diagram showing a medical image reading and/or diagnosis assistance apparatus that provides styling based on a user-preferred style based on the analysis result of a medical artificial neural network according to an embodiment of the present invention.

Referring to FIG. 6, the medical image reading and/or diagnosis assistance apparatus according to the present embodiment includes a computing system 600, and the computing system 600 includes at least one processor 630. The at least one processor 630 acquires or receives a first analysis result 612, obtained through the inference of the first artificial neural network 610 about the first medical image 650, via a communication interface 640. The at least one processor 630 may generate a second analysis result 660 reflecting a user-preferred style for the first medical image 650 based on the first analysis result 612, and may generate visualization information 662 that allows the first medical image 650 and the second analysis result 660 to be displayed on a screen based on the second analysis result 660. In this case, although not shown in FIG. 6, as in the embodiments of FIGS. 1, 2, and 5, the at least one processor 630 may generate the second analysis result 660 reflecting the user-preferred style for the first medical image 650 based on the first analysis result 612 in cooperation with a style learning model (not shown), and may generate visualization information 662 that allows the first medical image 650 and the second analysis result 660 to be displayed on a screen based on the second analysis result 660.

As in the embodiment of FIG. 5, the at least one processor 630 shown in FIG. 6 may provide a first user menu configured to receive information about whether a user has approved the second analysis result 660 displayed on a screen based on the second analysis result 660 onto the display screen via the user interface 670 together with the visualization information 662. The first user menu may be a user menu configured to allow the user to select either "confirm" or "reject."

The user interface 670 receives a user input 672, and transfers the user input 672 to the processor 630. When it is determined through the interpretation of the user input 672 that the user has approved the first analysis result 612 and the second analysis result 660, the at least one processor 630 may store the first analysis result 612 and the second analysis result 660 in a database 680 in association with the first medical image 650.

In FIG. 6, there is shown the embodiment in which the database 680 is located outside the computing system 600. The database 680 may be a database of a picture archiving and communication system (PACS) or a cloud-based database.

In the embodiment of FIG. 6, the computing system 600 may transmit and receive data via the external database 680 and the communication interface 640. The at least one processor 630 may store the first analysis result 612 and the second analysis result 660 in the database 680 in association with the first medical image 650 via the communication interface 640.

Since the other operations of the processor 630, the communication interface 640, the first artificial neural network 610, and the user interface 670 are the same as those of the processor 530, communication interface 540, first artificial neural network 510, and user interface 570 of FIG. 5, redundant descriptions thereof will be omitted.

Although the embodiment in which the database 680 is located outside the computing system 600 is shown in FIG. 6, it will be apparent to those skilled in the art that an embodiment in which a database (not shown) is located inside the computing system 600 may also be implemented according to another embodiment of the present invention.

In the embodiments of FIGS. 1 to 6, there are disclosed the medical image reading and/or diagnosis assistance apparatuses that improve medical image-based diagnoses and image analysis workflows in medical institutions and assist medical professionals in making image diagnoses.

In this case, a user may be a clinician or radiologist who is a medical professional. Meanwhile, depending on an object to be diagnosed, the user may be an assistant staff member who only has sufficient knowledge to check whether the image segmentation and detection results for a lesion are of a clinically preferred style at a medical site. In other words, even when a person does not have clinical knowledge but can check whether the segmentation of a specific area in an image has been accurately performed and also check whether results are of a clinically preferred style, the person may become a user of the present invention.

Furthermore, as shown in the embodiments of FIGS. 1 to 6, it is also important in terms of a workflow to provide a user menu configured to assist in implementing a correct analysis result by manually or semi-automatically re-analyzing an analysis result rejected by the user.

It is also important in terms of a workflow to store an analysis result approved by the user in a database of a PACS so that it can be used for an original diagnosis purpose (to be used for a diagnosis purpose in a medical institution).

Each of the first artificial neural networks 110, 210, 310, 410, 510 and 610 may provide at least one of image segmentation, lesion detection, and clinical diagnosis results for the first medical image 150, 250, 350, 450, 550 or 650 as the first analysis result 112, 212, 312, 412, 512 or 612. It is highly likely that a user-preferred style is reflected in the visualization of a boundary included in an image segmentation result, a lesion detection result, or the like. To clinically assist the facilitation of image diagnosis, a user-preferred style modification pattern regarding whether the image segmentation result, the lesion detection result, or the like further includes information about the surroundings of an anatomical structure or includes only a segmented or detected region may be tracked and trained on online. As a result, it may be possible to derive the second analysis result 160, 260, 360, 460, 560 or 560 that visualizes the first analysis result 112, 212, 312, 412, 512 or 612 in the user-preferred style without affecting the first artificial neural network 110, 210, 310, 410, 510 or 610. The user feedback on the second analysis result 160, 260, 360, 460, 560 or 560 itself may be reused for the training of the style learning model 120, 220 or 520 or second artificial neural network 320 or 420.

The first analysis result 112 and the second analysis result 160 that are approved by the user and stored in a database of a PACS or the like are data on a user-preferred style for the first analysis result 112. The user-preferred style may be used as descriptive information about the first artificial neural network 110 that derives the first analysis result 112. In other words, it may be used to compare computer-assisted diagnostic artificial neural networks (CAD engines, or segmentation engines) having different performances or to compare the advantages and disadvantages of CAD and segmentation engines. It may provide information on how an artificial neural network deals with an anatomical structure. It may be used as a means to help the understanding of the artificial neural network utilized at a medical site from a clinical point of view.

Each of the first artificial neural networks 110, 210, 310, 410, 510 and 610 shown in the embodiments of FIGS. 1 to 6 may have an image analysis function related to a plurality of diseases or lesions. In this case, each of the first artificial neural networks 110, 210, 310, 410, 510 and 610 may include a plurality of image analysis modules therein. The style learning model 120, 220 or 520 or second artificial neural network 320 or 420 of the present invention may hold learned information about user-preferred styles for a plurality of image analysis modules, a plurality of diseases, a plurality of lesions, or a plurality of image analysis results. In this case, each of the computing systems 100, 200, 300, 400, 500 and 600 of the present invention may generate the type of currently input analysis result and a lesion or disease associated with the currently input analysis result as context information, and may derive the second analysis result 160 in which an optimized user-preferred style has been reflected in according with the context information.

The factor that determines the second analysis result 160, 260, 360, 460, 560 or 660 based on the optimized user-preferred style is information included in the first medical image 150, 250, 350, 450, 550 or 650. This is formation included in the first analysis result 112, 212, 312, 412, 512 or 612 generated by the analysis of the first artificial neural network 110, 210, 310, 410, 510 or 610.

Furthermore, in order to visualize the first analysis result 112, 212, 312, 412, 512 or 612 and/or the second analysis result 160, 260, 360, 460, 560 or 660, the screen layout in which a plurality of reconstructed or reformatted images is displayed may be included in the visualization information 162, 262, 362, 462, 562 or 662. In this case, the visualization information 162, 262, 362, 462, 562 or 662 may include some of the information defined by a hanging protocol. Meanwhile, the visualization information 162, 262, 362, 462, 562 or 662 additionally includes information such as the direction of a view derived based on the medical image and the analysis result, as well as the type of reconstruction or reformat defined in the hanging protocol. Accordingly, the visualization information 162, 262, 362, 462, 562 or 662 may further include more specific information than the information defined in the hanging protocol.

Figure 7:
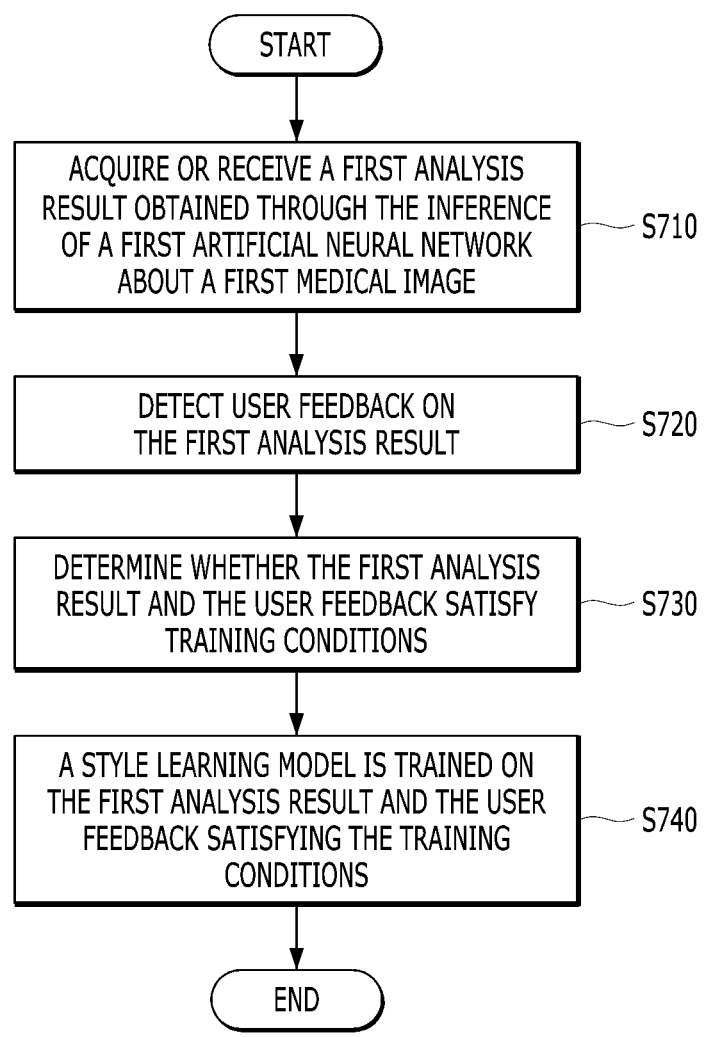
FIGS. 7 and 8 are operational flowcharts showing medical image reading and/or diagnosis assistance methods based on an artificial neural network according to embodiments of the present invention.
Figure 8:
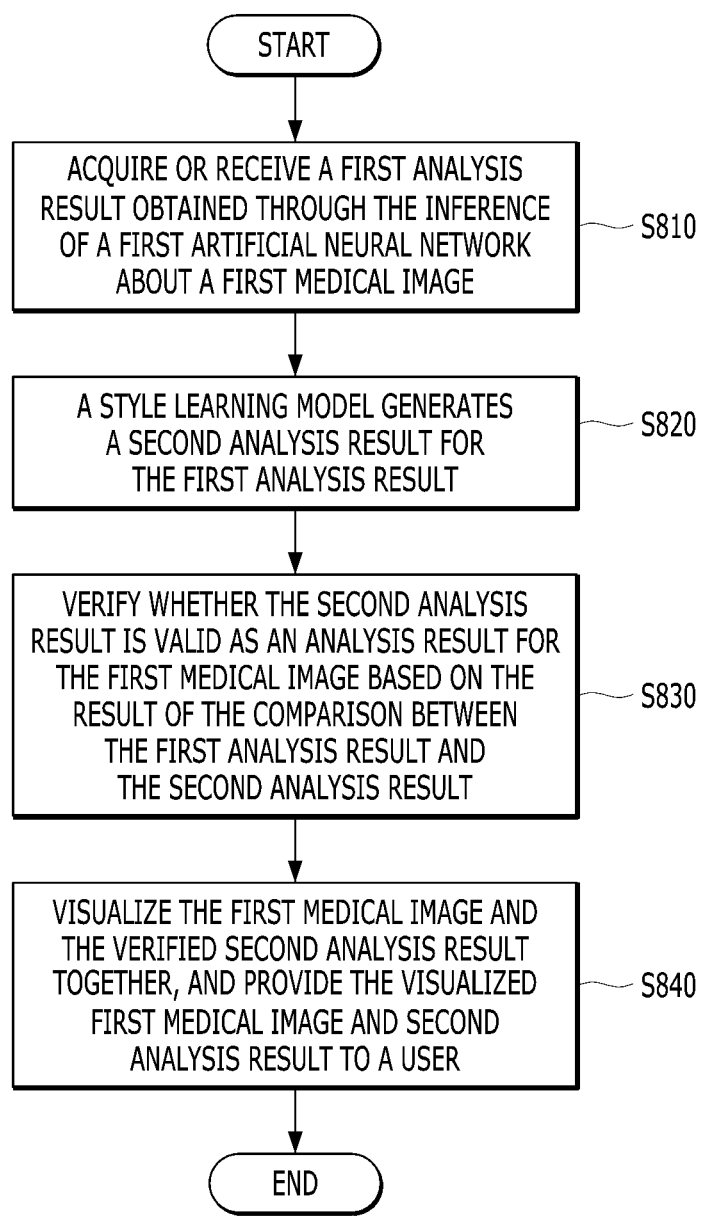

FIGS. 7 and 8 are operational flowcharts showing medical image reading and/or diagnosis assistance methods based on an artificial neural network according to embodiments of the present invention.

Referring to FIG. 7 together with FIGS. 1 to 6, the medical image reading and/or diagnosis assistance method based on an artificial neural network according to an embodiment of the present invention is performed by each of the computing systems 100, 200, 300, 400, 500 and 600, and the computing system 100, 200, 300, 400, 500 or 600 includes at least one processor 130, 230, 330, 430, 530 or 630. The medical image reading and/or diagnosis assistance method according to the present embodiment includes: step S710 of acquiring or receiving, by the at least one processor 130, 230, 330, 430, 530 or 630, the first analysis result 112, 212, 312, 412, 512 or 612 obtained through the inference of the first artificial neural network 110, 210, 310, 410, 510 or 610 for the first medical image 150, 250, 350, 450, 550 or 650; step S720 of detecting, by the at least one processor 130, 230, 330, 430, 530 or 630, user feedback on the first analysis result 112, 212, 312, 412, 512 or 612; step S730 of determining, by the at least one processor 130, 230, 330, 430, 530 or 630, whether the first analysis result 112, 212, 312, 412, 512 or 612 and user feedback for the first analysis result 112, 212, 312, 412, 512 or 612 satisfy training conditions; and step S740 of being trained on, by the style learning model 120, 220 or 520 or the second artificial neural network 320 or 420, the first analysis result 112, 212, 312, 412, 512 or 612 and the user feedback for the first analysis result 112, 212, 312, 412, 512 or 612 determined to satisfy the training conditions.

Referring to FIG. 8 together with FIGS. 1 to 6, the medical image reading and/or diagnosis assistance method based on an artificial neural network according to an embodiment of the present invention includes: step S810 of acquiring or receiving, by the at least one processor 130, 230, 330, 430, 530 or 630, the first analysis result 112, 212, 312, 412, 512 or 612 obtained through the inference of the first artificial neural network 110, 210, 310, 410, 510 or 610 for the first medical image 150, 250, 350, 450, 550 or 650; step S820 of generating, by the style learning model 120, 220 or 520 or second artificial neural network 320 or 420, the second analysis result 160, 260, 360, 460, 560 or 660 reflecting a user-preferred style for the first medical image 150, 250, 350, 450, 550 or 650 based on the first analysis result 112, 212, 312, 412, 512 or 612; step S830 of, verifying, by at least one processor 130, 230, 330, 430, 530 or 630, whether the second analysis result 160, 260, 360, 460, 560 or 660 is a valid analysis result for the first medical image 150, 250, 350, 450, 550 or 650 based on the result of comparison between the first analysis result 112, 212, 312, 412, 512 or 612 and the second analysis result 160, 260, 360, 460, 560 or 660; and step S840 of visualizing, by the at least one processor 130, 230, 330, 430, 530 or 630, the first medical image 150, 250, 350, 450, 550 or 650 and the second analysis result 160, 260, 360, 460, 560 or 660 so that the first medical image 150, 250, 350, 450, 550 or 650 and the second analysis result 160, 260, 360, 460, 560 or 660 are displayed on a screen based on the second analysis result 160, 260, 360, 460, 560 or 660.

At step S840 of visualizing the first medical image 150, 250, 350, 450, 550 or 650 and the second analysis result 160, 260, 360, 460, 560 or 660, the at least one processor 130, 230, 330, 430, 530 or 630 may visualize the first medical image 150, 250, 350, 450, 550 or 650, the first analysis result 112, 212, 312, 412, 512 or 612, and the second analysis result 160, 260, 360, 460, 560 or 660 so that the first user menu configured to receive information about whether a user has approved the first analysis result 112, 212, 312, 412, 512 or 612 displayed on a screen based on the second analysis result 160, 260, 360, 460, 560 or 660 and/or the second analysis result 160, 260, 360, 460, 560 or 660 is included therein.

There may be further included the step of, when the user has not approved the second analysis result 160, 260, 360, 460, 560 or 660, providing, by the at least one processor 130, 230, 330, 430, 530 or 630, the second user menu configured to generate the third analysis result replacing the second analysis result 160, 260, 360, 460, 560 or 660 for the first medical image 150, 250, 350, 450, 550 or 650 independently of the second analysis result 160, 260, 360, 460, 560 or 660.

The second user menu may be a user menu configured to manually or semi-automatically generate the third analysis result.

At step S820 of generating the second analysis result 160, 260, 360, 460, 560 or 660, the second analysis result 160, 260, 360, 460, 560 or 660 may be generated based on at least one of image segmentation, lesion detection, and clinical diagnosis results for the first medical image 150, 250, 350, 450, 550 or 650 included in the first analysis result 112, 212, 312, 412, 512 or 612.

The second analysis result 160, 260, 360, 460, 560 or 660 may be visualized together with at least one of at least one view of the first medical image 150, 250, 350, 450, 550 or 650 associated with the first analysis result 112, 212, 312, 412, 512 or 612, at least part of the first medical image 150, 250, 350, 450, 550 or 650 selected from the first medical image 150, 250, 350, 450, 550 or 650 based on the degree of association with the first analysis result 112, 212, 312, 412, 512 or 612, the result of the reconstruction of the first medical image 150, 250, 350, 450, 550 or 650, and the result of the reformatting of the first medical image 150, 250, 350, 450, 550 or 650.

Referring to FIGS. 7 and 8 together with FIGS. 3 and 4, the computing system 300 or 400 may further include the second artificial neural network 320 or 420 that has received a plurality of pieces of user feedback selected from among a plurality of fourth analysis results for a plurality of second medical images by a professional and has been trained on the function of generating a styling modification reflecting a user-preferred style based on the association between a plurality of fourth analysis results and a plurality of pieces of user feedback. The training of the second artificial neural network 320 or 420 on the user-preferred style may be further enhanced by steps S710, S720, S730 and S740 shown in FIG. 7. In this case, at step S820 of generating the second analysis result 360 or 460 based on the first analysis result 312 or 412, the at least one processor 330 or 430 may input the first analysis result 312 or 412 to the second artificial neural network 320 or 420, and may control the second artificial neural network 320 or 420 so that the second artificial neural network 320 or 420 acquires the second analysis result 360 or 460 through the inference of the second artificial neural network 320 or 420.

Referring to FIGS. 7 and 8 together with FIGS. 1, 3, 5 and 6, at each of steps S710 and S810 of acquiring or receiving, by at least one processor 130, 330, 530 or 630, the first analysis result 112, 312, 512 or 612 obtained through the inference of the first artificial neural network 110, 310, 510 or 610 about the first medical image 150, 350, 550 or 650, the at least one processor 130, 330, 530 or 630 may acquire or receive the first analysis result 112, 312, 512 or 612 via the communication interface 140, 340, 540 or 640 that transmits and receives data to and from the first artificial neural network 110, 310, 510 or 610 outside the computing system 100, 300, 500 or 600.

Referring to FIGS. 8 and 6 together, there may be further included the step of, when the user approves the second analysis result 660, storing, by at least one processor 630, the first analysis result 612 and the second analysis result 660 in the database 680 in association with the first medical image 650.

In this case, the at least one processor 630 may store the first analysis result 612 and the second analysis result 660 in the database 680 in association with the first medical image 650 via the communication interface 640 via which the at least one processor 630 transmits and receives data to and from the database 680 outside the computing system 600.

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the artificial neural network-based medical image reading and/or diagnosis assistance system of the present invention, the first artificial neural network configured to generate a first analysis result and the style learning model configured to receive and be trained on user feedback may be separated from each other. Accordingly, the present invention is expected to provide additional performance improvement based on user feedback without directly affecting the existing performance of the first artificial neural network as a CAD engine.

According to the present invention, a style learning model may be trained on a styling pattern preferred by a user, and may provide a second analysis result reflecting a user-preferred style corresponding to a first analysis result of the first artificial neural network.

According to the present invention, a user-preferred styling pattern may be trained on by a style learning model which is constructed and is trained independently of a first artificial neural network-based CAD engine.

According to the present invention, user feedback for a first analysis result may be detected, it may be determined whether to allow a style learning model to be trained on the user feedback, and the style learning model may be trained on user feedback determined to be trained on by the style learning model and a first analysis result corresponding to the user feedback.

According to the present invention, there may be provided a criterion for determining whether to allow a style learning model to be trained on user feedback on a first analysis result.

According to the present invention, it may be evaluated whether a first analysis result is accepted by a user, who is a doctor, based on user feedback on the first analysis result, and a style learning model may be trained on the first analysis result and the user feedback when the user accepts the first analysis result.

According to the present invention, when a second analysis result reflecting a user-preferred style for a first analysis result is generated, the information of the inner layer of a first artificial neural network which provides the first analysis result may be partially used.

According to the present invention, when a second analysis result reflecting a user-preferred style for the first analysis result is generated, a first medical image, i.e., the basis of a first analysis result, may be received, and a style learning model may provide a detailed styling result based on the context information, such as the body part and the organ, of the first medical image. In this case, the style learning model may be trained on a detailed user-preferred style based on the context information.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. An artificial neural network-based medical image diagnosis assistance apparatus for assisting in diagnosing a medical image based on a medical artificial neural network, the medical image diagnosis assistance apparatus comprising a computing system, the computing system comprising at least one processor, wherein the at least one processor is configured to:
acquire or receive a first analysis result obtained through an inference of a first artificial neural network about a first medical image;
detect user feedback on the first analysis result input by a user;
determine whether the first analysis result and the user feedback including a modification of the first analysis result satisfy training conditions to train a style learning model, based on at least one of a similarity between a user-modified first analysis result generated based on the user feedback on the first analysis result and the first analysis result, a size of a difference region between the first analysis result and the user-modified first analysis result, a shape of the difference region, or a distribution of brightness values of the difference region in the first medical image; and
transfer the first analysis result and the user feedback satisfying the training conditions to the style learning model so that the style learning model is trained on the first analysis result and the user feedback.

2. The artificial neural network-based medical image diagnosis assistance apparatus of claim 1, wherein the at least one processor is further configured to determine the similarity between the user-modified first analysis result and the first analysis result based on at least one of a Hausdorff distance between a first set of pixels or voxels included in a first boundary of the first analysis result and a modified first set of pixels or voxels included in a user-modified first boundary of the user-modified first analysis result and a ratio between a first area or first volume of an area surrounded by the first boundary and a modified first area or modified first volume of an area surrounded by the user-modified first boundary.

3. The artificial neural network-based medical image diagnosis assistance apparatus of claim 1, wherein the at least one processor is further configured to:
evaluate whether the user accept the first analysis result based on the user feedback on the first analysis result; and
when the user accepts the first analysis result, determine that the first analysis result and the user feedback satisfy the training conditions.

4. The artificial neural network-based medical image diagnosis assistance apparatus of claim 1, wherein the at least one processor is further configured to:
receive a prediction result predicting whether the user will accept the first analysis result; and
determine whether the first analysis result and the user feedback satisfy the training conditions based on the prediction result.

5. The artificial neural network-based medical image diagnosis assistance apparatus of claim 1, wherein the at least one processor is further configured to:
receive a preliminary first analysis result, which is an output before a final layer inside the first artificial neural network, together with the first analysis result; and
transfer the preliminary first analysis result to the style learning model together with the first analysis result and the user feedback satisfying the training conditions, and control training of the style learning model so that the style learning model is trained on relationships among the first analysis result, the preliminary first analysis result, and the user feedback.

6. The artificial neural network-based medical image diagnosis assistance apparatus of claim 1, wherein the at least one processor is further configured to controls training of the style learning model so that the style learning model is trained on a relationship between the first analysis result and the user feedback based on context information including body part and organ information included in the first medical image.

7. The artificial neural network-based medical image diagnosis assistance apparatus of claim 1, wherein:
the style learning model is a second artificial neural network, and the computing system further comprises the second artificial neural network; and
the at least one processor is further configured to:
input the first analysis result and the user feedback satisfying the training conditions to the second artificial neural network; and
control training of the second artificial neural network so that the second artificial neural network is trained on a relevance between the first analysis result and the user feedback satisfying the training conditions.

8. The artificial neural network-based medical image diagnosis assistance apparatus of claim 1, wherein:
the computing system further comprises a communication interface configured to transmit and receive data to and from the first artificial neural network outside the computing system; and
the at least one processor is further configured to acquire and receive the first analysis result obtained through the inference of the first artificial neural network about the first medical image via the communication interface.

9. The artificial neural network-based medical image diagnosis assistance apparatus of claim 1, wherein the at least one processor is further configured to:
provide a first user menu configured to receive information about whether the user has approved the first analysis result for the first medical image; and
when the user has approved the first analysis result via the first user menu, determine that the first analysis result and the user feedback satisfy the training conditions.

10. An artificial neural network-based medical image diagnosis assistance method that is performed by a computing system, the computing system comprising at least one processor, the artificial neural network-based medical image diagnosis assistance method comprising:
acquiring or receiving, by the at least one processor, a first analysis result obtained through an inference of a first artificial neural network about a first medical image;
detecting, by the at least one processor, user feedback on the first analysis result input by a user;
determining, by the at least one processor, whether the first analysis result and the user feedback including a modification of the first analysis result satisfy training conditions to train a style learning model, based on at least one of a similarity between a user-modified first analysis result generated based on the user feedback on the first analysis result and the first analysis result, a size of a difference region between the first analysis result and the user-modified first analysis result, a shape of the difference region, or a distribution of brightness values of the difference region in the first medical image; and
transferring, by the at least one processor, the first analysis result and the user feedback satisfying the training conditions to the style learning model so that the style learning model is trained on the first analysis result and the user feedback.

* * * * *